United States Patent
Hedberg et al.

(10) Patent No.: US 7,353,061 B2
(45) Date of Patent: Apr. 1, 2008

(54) BIVENTRICULAR STIMULATION DEVICE WITH SHORTENED INTER-VENTRICULAR DELAY

(75) Inventors: Sven-Erik Hedberg, Kungsängen (SE); Anders Björling, Järfälla (SE); Per Lagercrantz, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 10/573,281

(22) PCT Filed: Sep. 25, 2003

(86) PCT No.: PCT/SE03/01494

§ 371 (c)(1),
(2), (4) Date: Mar. 23, 2006

(87) PCT Pub. No.: WO2005/028030

PCT Pub. Date: Mar. 31, 2005

(65) Prior Publication Data
US 2007/0055312 A1  Mar. 8, 2007

(51) Int. Cl.
*A61N 1/00* (2006.01)
(52) U.S. Cl. .............................. 607/9; 607/25; 607/115; 607/119
(58) Field of Classification Search ...................... 607/9
See application file for complete search history.

(56) References Cited

U.S. PATENT DOCUMENTS 6,148,234 A  11/2000  Struble 6,587,723 B1  7/2003  Sloman et al.
6,915,164 B2 *  7/2005  Bradley et al. ............... 607/29
2002/0082650 A1  6/2002  Stahmann et al.

FOREIGN PATENT DOCUMENTS

| EP | 1 155 711 | 11/2001 |
| EP | 1 155 712 | 11/2001 |
| WO | WO 01/74441 | 10/2001 |

* cited by examiner

*Primary Examiner*—Carl Layno
*Assistant Examiner*—Brian T. Gedeon
(74) *Attorney, Agent, or Firm*—Schiff Hardin LLP

(57) ABSTRACT

A biventricular cardiac stimulation device has a pulse generator for delivering stimulation pulses at least to the ventricles of a patient's heart. An evoked response detector has independent first and second ventricular sensing channels for ventricular evoked response detection in the ventricles. The pulse generator is controlled to deliver stimulation pulses to the second ventricle with a VV time delay after delivery of a stimulation pulse to the first-stimulated ventricle, the VV time delay being shorter than an evoked response detection time window that follows delivery of the stimulation pulse to the first-stimulated ventricle. An evoked response detector closes the evoked response detection window, or discards detections therein, in response to the emission of a stimulation pulse to the second-stimulated ventricle during the evoked response detection time window of the first-stimulated ventricle.

12 Claims, 5 Drawing Sheets

BIVENTRICULAR STIMULATION DEVICE WITH SHORTENED INTER-VENTRICULAR DELAY

BACKGROUND OF THE INVENTION

1. Field of the Invention

The present invention relates to a biventricular stimulation device a pulse generator for delivering stimulation pulses at least to the ventricles of a patient's heart, and an evoked response detector having first and second, independent ventricular sensing channels for ventricular evoked response detection in the ventricles, the pulse generator being controlled to deliver the stimulation pulses to the second ventricle with a VV time delay after stimulation pulse delivery to the first stimulated ventricle that is shorter than an evoked response detection time window following delivery of a stimulation pulse to the first stimulated ventricle.

2. Description of the Prior Art

In the following, the ventricle set to be stimulated first is referred to as "the first ventricle", and the ventricle that is set to be stimulated second as "the second ventricle". Even though there is a difference both in stimulation threshold and amplitude of intrinsic signals for the left and the right ventricles, there will be no difference in stimulation strategy if the left or right ventricle is stimulated first. The terms "first" and "second" are only related to the programming of the stimulation device.

In a biventricular pacemaker with a comparatively short VV time delay of less than e.g. 40 msec the evoked response time window, ERW, for the first stimulated ventricle will be interrupted by a stimulation pulse delivered to the second ventricle, i.e. the last stimulated ventricle of the heart. Thus beat-to-beat evoked response, ER, detection on the first ventricle is impossible with such a short VV time delay.

However, in some cases ER detection is possible on the first ventricle regardless of a short VV time delay as mentioned above.

SUMMARY OF THE INVENTION

An object of the present invention is to utilize this the above-noted possibility for providing a biventricular stimulation device with improved ER detection in the first ventricle despite a short VV time delay.

The above object is achieved in accordance with the present invention in a biventricular cardiac stimulation device of the type initially described, wherein the evoked response detector closes the evoked response detection time window, or discards detections therein, in response to the emission of stimulation pulse to the second ventricle during the evoked response detection time window of the first stimulated ventricle.

For a normal stimulation pattern in biventricular stimulation devices the left ventricle is the first stimulated heart chamber and the right ventricle the second one, since LBBB is much more frequent than RBBB. An intrinsic R wave originating from e.g. a conducted P wave will thus be sensed in the right ventricle, probably shortly after the stimulation pulse is delivered to the left ventricle. In the stimulation device according to the invention an ERW is always started after each one of the stimulation pulses to the first ventricle even when a short VV time delay is programmed. The evoked response detector of the stimulation device is then arranged to close the ERW or discard detections therein in response to the emission of a stimulation pulse to the second ventricle during the ERW of the first stimulated ventricle. Thus, only if there is emitted a stimulation pulse to the second ventricle no decision concerning capture or loss of capture of the first ventricle will be taken. An important feature of the stimulation device according to the invention is that the evoked response detector is provided with first and second, independent ventricular sensing channels for ventricular evoked response detection in the respective ventricles, as in for instance Epic HF.

In an embodiment of the device according to the invention an inhibiting unit is provided for inhibiting stimulation in the second ventricle in response to the detection of a sensed intrinsic cardiac event therein, and the VV time delay is less than 40 msec, preferably in the range of 10-30 msec, and the duration of ERW is in the range of 40-100 msec.

DESCRIPTION OF THE PREFERRED EMBODIMENTS

Figure 1:
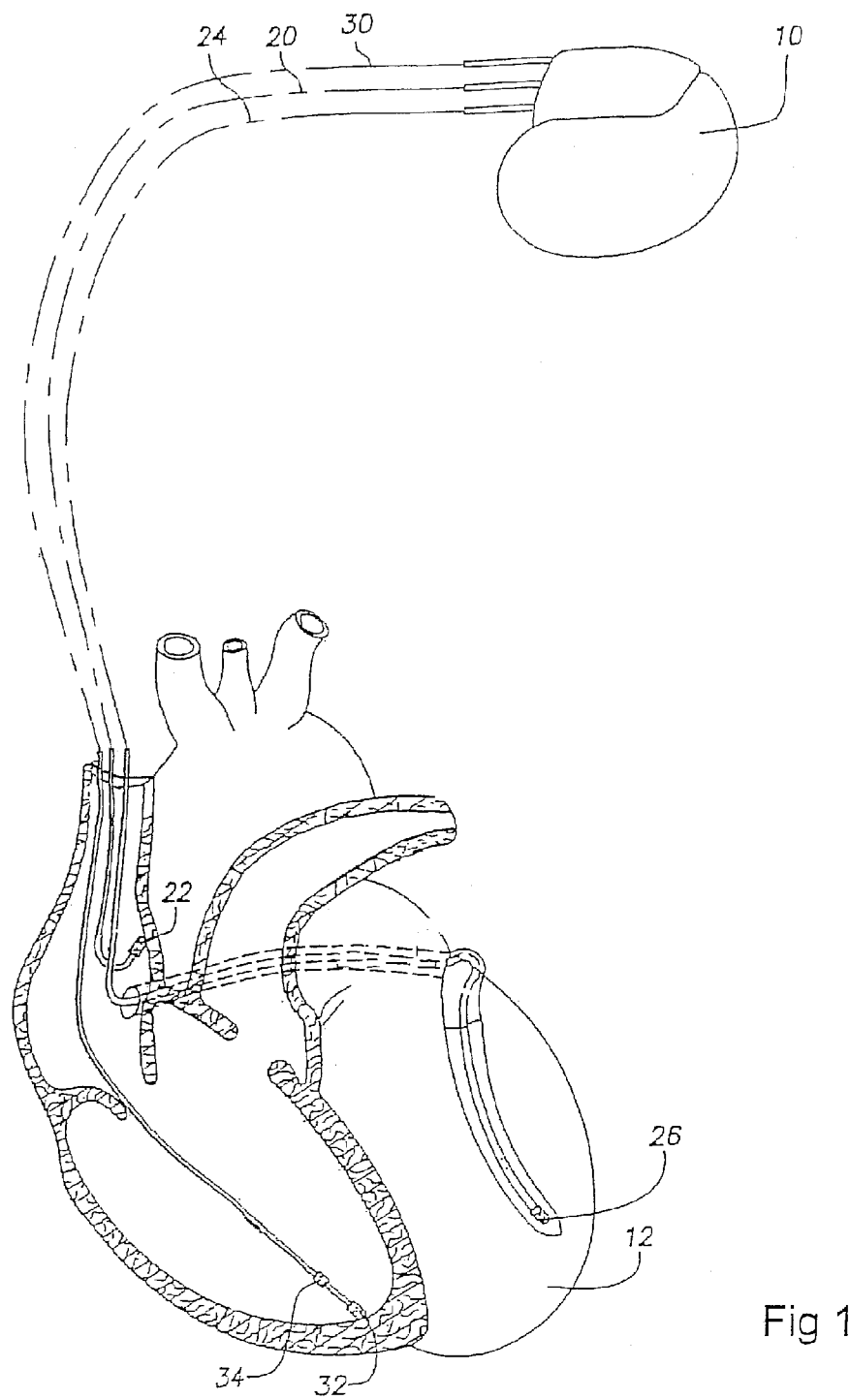
FIG. 1 illustrates typical placements in the heart of the leads of a biventricular stimulation device according to the invention, also having an implanted atrial lead.

FIG. 1 shows a heart stimulation device in the form of a pacemaker 10 having an atrial lead 20 and two ventricular leads 24, 30 for stimulating and independently sensing in the left atrium and the ventricles of the heart 12. FIG. 1 shows typical positions for an atrial electrode 22, right ventricular electrodes 32, 34 and a left ventricular electrode 26 placed in the coronary sinus. The biventricular pacing lead configuration has a unipolar left ventricular lead 24, 26 and a bipolar right ventricular lead 30, 32, 34. By implanting an atrial lead 20, 22, AV synchronous pacing modes are also possible.

Figure 2:
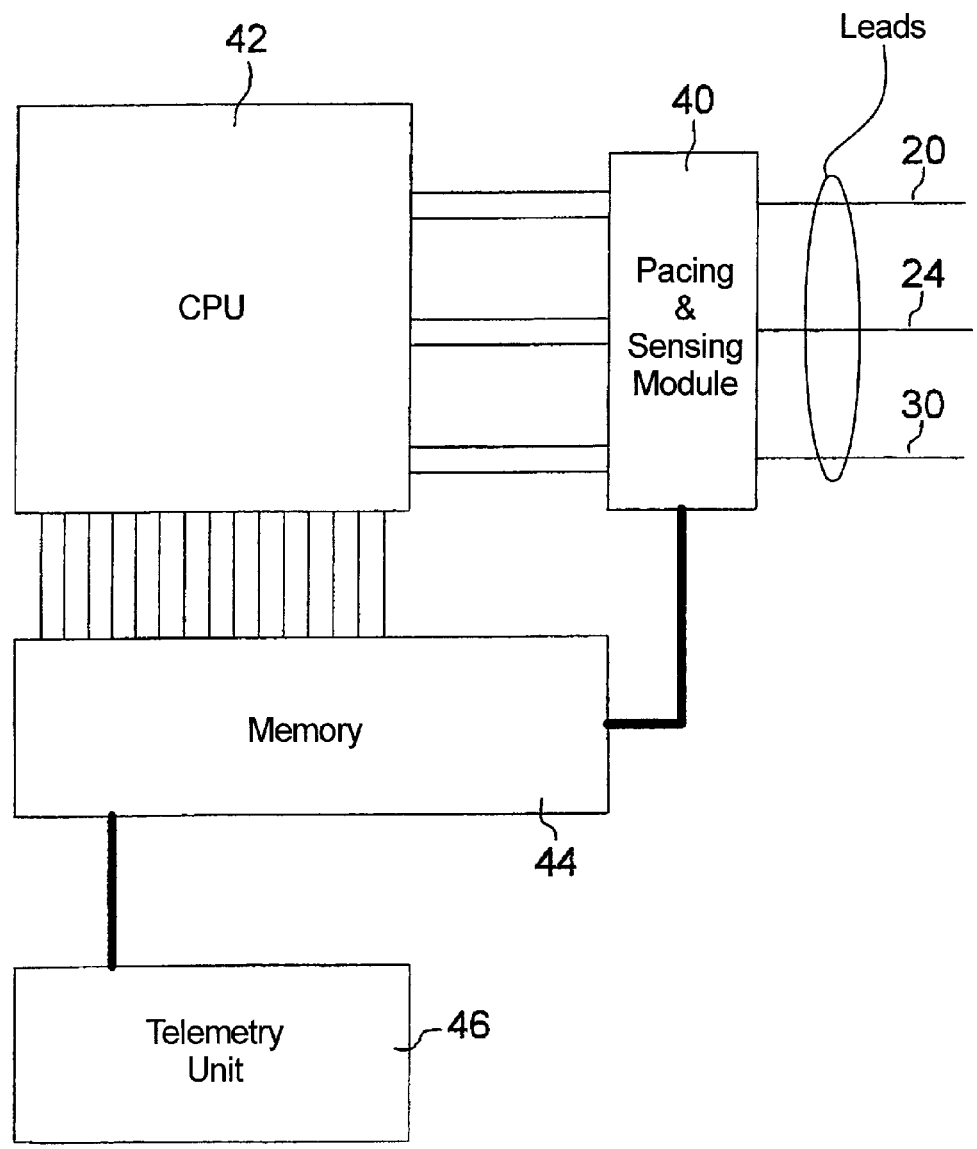
FIG. 2 is a block diagram of the basic components of a stimulation device such as the pacemaker shown in FIG. 1.

FIG. 2 is a block diagram of the basic units of the pacemaker 10 in FIG. 1. The implanted leads 20, 24, 30 in FIG. 2 are connected to an input/output stage 40 in the pacemaker 10. The stage 40 comprises a pacing and a sensing module as will be further described in connection with FIG. 3. The operation on the pacemaker is controlled by a CPU 42. The pacemaker also includes a memory 44 for storing information about e.g. how the stimulation threshold has changed over time, how much stimulation has been given, energy consumption etc. which is read out at follow ups. A telemetry unit 46 is provided for the communication between the implanted pacemaker and an external programmer.

Figure 3:
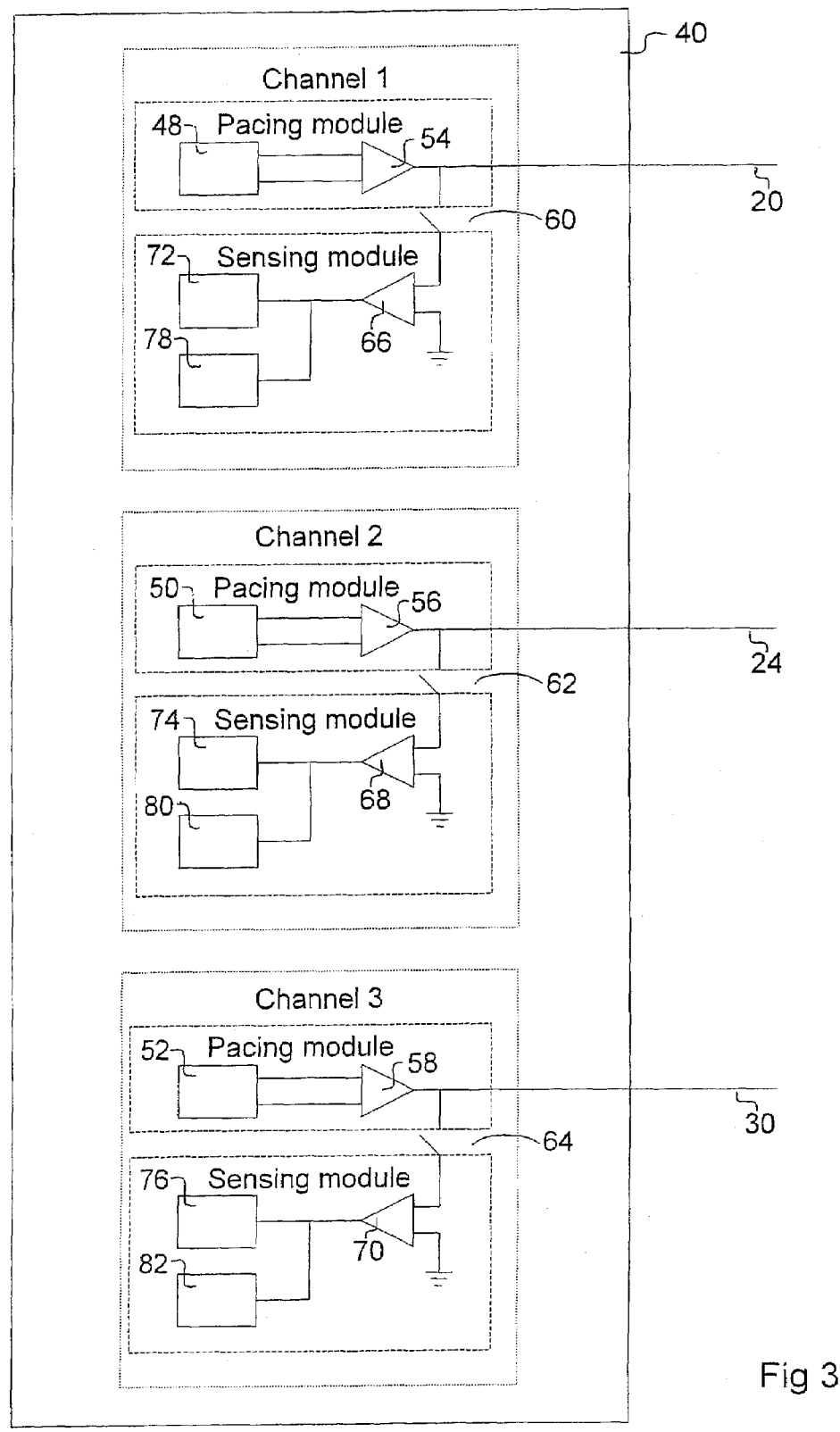
FIG. 3 is a block diagram illustrating the input/output stage in FIG. 2 in more detail.

The input/output stage 40 to which the leads 20, 24 and 30 are connected is shown in a larger scale in FIG. 3. Thus this stage 40 has three channels, one lead 20, 24, and 30 respectively being connected to each of the channels. Each channel comprises a pacing module and a sensing module, and each pacing module includes a pacing stage 48, 50, 52 connected to an amplifier 54, 56, 58. The leads 20, 24, 30 are connected to the outputs of the amplifiers 54, 56, 58 for delivering stimulation pulses to the patient's heart as controlled from the CPU 42.

The leads 20, 24, 30 are also used for sensing signals in the heart and can be connected, via switches 60, 62, 64 to the sensing module of each channel. Each sensing module includes an amplifier 66, 68, 70 in which sensed signals are amplified and the amplified signals are then supplied to an event detector 72, 74, 76 and ER detector 78, 80, 82 for detecting possible evoked response of the heart. It is important that the three channels for stimulation and sensing are separated.

The switches 60, 62, 64 are controlled to disconnect all sensing modules whenever a stimulation pulse is delivered on anyone of the channels to avoid that the stimulation give rise to disturbances and saturation in the sensing modules. The switches 60, 62, 64 are controlled to otherwise connect the sensing modules to their respective lead 20, 24, 30.

The CPU 42 comprises an inhibiting means for inhibiting stimulation in the second ventricle, e.g. the right ventricle, in response to the detection by the associated sensing module of a sensed cardiac event therein within the VV time delay. The evoked response detector is arranged to close the evoked response detection time window of the first ventricle or discard detections therein in response to the emission of a stimulation pulse to the second ventricle, during the evoked response detection time window of the first stimulated ventricle.

Figure 4:
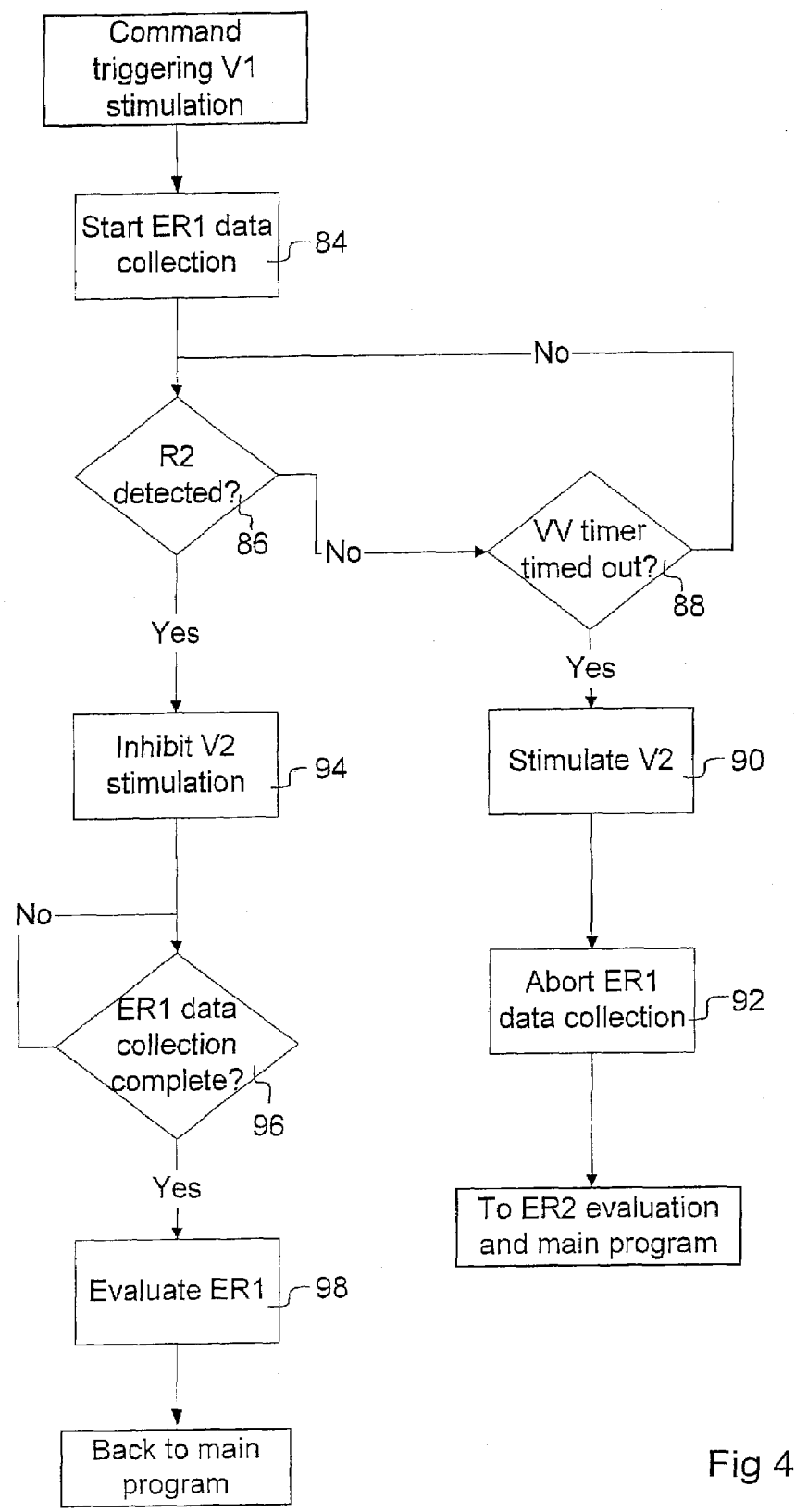
FIG. 4 is a flow chart illustrating the operation of the pacemaker shown in FIGS. 1, 2 and 3, in accordance with the present invention.

The operation of the above embodiment of the stimulation device according to the invention is illustrated by a flow diagram in FIG. 4. Thus a command is given triggering stimulation of the first ventricle V1. Collection of data for evoked response, ER, detection in the first ventricle is started, block 84. If no cardiac event, like an R wave, R2, is detected in the second ventricle within the predetermined VV time delay, blocks 86 and 88, a stimulation pulse is delivered to the second ventricle V2, block 90. The connection of ER 1 data is then aborted, block 92, and possible resulting evoked response ER 2 is evaluated and the main procedure is continued.

If a cardiac event in the second ventricle, R2, is detected before the expire of the W time delay stimulation to the second ventricle, V2, is inhibited by the inhibiting means, block 94. If the collection of evoked response data ER1 from the first ventricle is then completed, block 96, these data are evaluated for detection of possible evoked response, block 98, otherwise this ER1 data collection is repeated or continued till completion, cf. block 96. After terminated evoked response detection in the first ventricle the basic procedure is repeated.

Figure 5:
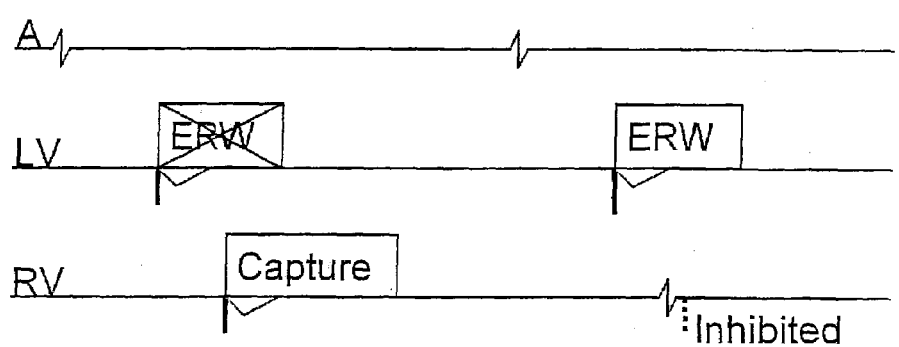
FIG. 5 is a timing diagram for further explaining the operation of the biventricular stimulation device in accordance with the present invention.

An example of the operation of the device according to the invention is also illustrated by a timing diagram in FIG. 5. Line A relates to the atrium and lines LV and RV to the left and right ventricles respectively. P-waves are shown at 100, 102. The left ventricle LV is first stimulated at 104 and an evoked response detection time window ERW 106 is following this stimulation pulse 104. If a stimulation pulse 107 is delivered to the second ventricle RV the ERW of the first ventricle 106 will be closed and the results discarded. No decision concerning capture or loss of capture will then be taken.

The stimulation pulse 107 to the right second ventricle is followed by-an ERW 108 for detection of capture or loss of capture in normal way.

If an intrinsic R wave 110 is detected in the second ventricle RV, e.g. originating from a conducted P wave 102, this intrinsic R wave 110 will be sensed in the second ventricle RV, probably shortly after the stimulation pulse in the first ventricle LV. The sensed R wave 110 in the second ventricle RV will then control the inhibiting means to inhibit the second stimulation pulse 114 and ER detection in the associated ERW 112 of the first ventricle LV is performed. In summary, if a RV stimulation pulse is emitted during the LV evoked response detection time window no ER detection is performed in LV, else ER detection will always be performed in LV.

The example above relates to patients for which the LV stimulation is programmed to come first, e.g. most LBBB patients. For most RBBB patients the situation will be analogous with first and second ventricles shifted Although modifications and changes may be suggested by those skilled in the art, it is the invention of the inventors to embody within the patent warranted heron all changes and modifications as reasonably and properly come within the scope of their contribution to the art.

We claim as our invention:

1. A biventricular cardiac stimulation device comprising:
   a pulse generator configured to interact respectively with ventricles of a heart to deliver stimulation pulses to each of the ventricles;
   a control unit connected to the pulse generator that operates the pulse generator to emit a stimulation pulse to a first-stimulated ventricle, followed by a VV time delay, followed by a stimulation pulse to a second-stimulated ventricle;
   an evoked response detector configured to interact with the ventricles and having independent, first and second ventricular sensing channels that detect ventricular evoked response in the respective ventricles, said evoked response detector searching for an evoked response following delivery of a stimulation pulse to said first-stimulated ventricle in an evoked response detection time window;
   said control unit setting said VV time delay to be shorter than said evoked response detection time window; and
   said evoked response detector closing said evoked response detecting time window, or discarding detections therein, in response to emission of the stimulation pulse to the second-stimulated ventricle during said evoked response detection time window following said first-stimulated ventricle.

2. A biventricular cardiac stimulation device as claimed in claim 1, comprising an inhibiting unit that inhibits stimulation of said second-stimulated ventricle in response to detection, by said evoked response detector, of a sensed intrinsic cardiac event in said second-stimulated ventricle.

3. A biventricular cardiac stimulation device as claimed in claim 1 wherein said control unit sets said VV time delay to be less than 40 msec.

4. A biventricular cardiac stimulation device as claimed in claim 3 wherein said control unit sets said VV time delay in a range between 10 and 30 msec.

5. A biventricular cardiac stimulation device as claimed in claim 1 wherein said evoked response detector sets said evoked response detection time window for said first-stimulated ventricle to be in a range between 40 and 100 msec.

6. A method for biventricular cardiac stimulation comprising the steps of:
   with an implanted pulse generator, automatically delivering stimulation pulses respectively to the ventricles of a heart;
   automatically controlling operation of the pulse generator to emit a stimulation pulse to a first-stimulated ventricle, followed by a VV time delay, followed by a stimulation pulse to a second-stimulated ventricle;

with an implanted evoked response detector having independent, first and second ventricular sensing channels, automatically detecting ventricular evoked response in the respective ventricles by searching for an evoked response following delivery of a stimulation pulse to said first-stimulated ventricle in an evoked response detection time window;

with said control unit, setting said VV time delay to be shorter than said evoked response detection time window; and automatically causing said evoked response detector to close said evoked response detecting time window, or to discard detections therein, in response to emission of the stimulation pulse to the second-stimulated ventricle during said evoked response detection time window following said first-stimulated ventricle.

7. A method as claimed in claim 6, comprising inhibiting stimulation of said second-stimulated ventricle in response to detection, by said evoked response detector, of a sensed intrinsic cardiac event in said second-stimulated ventricle.

8. A method as claimed in claim 6 comprising setting said VV time delay to be less than 40 msec.

9. A method as claimed in claim 8 comprising setting said VV time delay in a range between 10 and 30 msec.

10. A method as claimed in claim 9 comprising setting said evoked response detection time window for said first-stimulated ventricle to be in a range between 40 and 100 msec.

11. A method as claimed in claim 8 comprising setting said evoked response detection time window for said first-stimulated ventricle to be in a range between 40 and 100 msec.

12. A method as claimed in claim 6 comprising setting said evoked response detection time window for said first-stimulated ventricle to be in a range between 40 and 100 msec.

* * * * *